(12) United States Patent
Watkins et al.

(10) Patent No.: US 6,623,638 B2
(45) Date of Patent: Sep. 23, 2003

(54) HEMODIALYZER HAVING IMPROVED DIALYSATE PERFUSION

(75) Inventors: Randolph H. Watkins, Wonder Lake, IL (US); James S. Slepicka, Spring Grove, IL (US); Michael R. Prisco, Geneva, IL (US)

(73) Assignee: Baxter International Inc., Deerfield, IL (US)

( * ) Notice: Subject to any disclaimer, the term of this patent is extended or adjusted under 35 U.S.C. 154(b) by 62 days.

(21) Appl. No.: 09/871,864

(22) Filed: Jun. 1, 2001

(65) Prior Publication Data

US 2003/0080047 A1 May 1, 2003

(51) Int. Cl.⁷ ............... B01D 63/02; B01D 61/28
(52) U.S. Cl. .............. 210/321.79; 210/321.6; 210/321.72; 210/321.8; 210/321.88; 210/321.89; 210/456; 210/500.23
(58) Field of Search .......... 210/321.6, 321.72, 210/321.79, 321.8, 321.88, 321.89, 450, 456, 500.23

(56) References Cited

U.S. PATENT DOCUMENTS

| | | |
|---|---|---|
| 4,141,835 A | 2/1979 | Schäel et al. |
| 4,201,673 A | 5/1980 | Kanno et al. |
| 4,202,776 A | 5/1980 | Joh |
| 4,219,426 A | 8/1980 | Spekle et al. |
| 4,220,535 A | 9/1980 | Leonard |
| 4,237,013 A | 12/1980 | Yamazaki et al. |
| 4,242,203 A | 12/1980 | Amicel et al. |
| 4,396,510 A * | 8/1983 | Hsei ............ 210/321.3 |
| 4,572,724 A | 2/1986 | Rosenberg et al. |
| 4,639,353 A | 1/1987 | Takemura et al. |
| 4,724,900 A | 2/1988 | Baurmeister et al. |
| 4,876,012 A | 10/1989 | Kopp et al. |
| 4,911,846 A | 3/1990 | Akasu et al. |
| 4,919,802 A | 4/1990 | Katsura |
| 5,053,130 A | 10/1991 | Raff et al. |
| 5,072,498 A | 12/1991 | Raff et al. |
| 5,084,244 A | 1/1992 | Muramoto |
| 5,139,741 A | 8/1992 | Hagiwara |
| 5,147,544 A | 9/1992 | Vescovini |
| 5,160,615 A | 11/1992 | Takagi et al. |
| 5,240,612 A | 8/1993 | Grangeon et al. |
| 5,346,621 A | 9/1994 | Haworth et al. |
| 5,352,361 A | 10/1994 | Prasad et al. |
| 5,500,134 A | 3/1996 | Chahine |
| 5,525,144 A | 6/1996 | Gollan |
| 5,605,630 A | 2/1997 | Shibata |
| 5,618,425 A | 4/1997 | Mitamura et al. |
| 5,626,759 A | 5/1997 | Krantz et al. |
| 5,632,894 A | 5/1997 | White et al. |
| 5,700,372 A | 12/1997 | Takesawa et al. |
| 5,782,791 A | 7/1998 | Peterson et al. |
| 5,798,041 A | 8/1998 | Zuk, Jr. |
| 5,817,279 A | 10/1998 | Eilers et al. |
| 5,830,370 A | 11/1998 | Maloney, Jr. et al. |
| 5,919,369 A | 7/1999 | Ash |
| 5,938,940 A | 8/1999 | Zuk, Jr. |
| 6,030,539 A | 2/2000 | Zuk, Jr. |
| 6,074,559 A | 6/2000 | Hahmann et al. |
| 6,113,782 A | 9/2000 | Leonard |
| 6,176,904 B1 | 1/2001 | Gupta |

FOREIGN PATENT DOCUMENTS

| | | |
|---|---|---|
| DE | 2839937 A1 | 4/1980 |
| EP | 0 968 730 | 1/2000 |
| WO | WO 93/13941 | 7/1993 |
| WO | 98/22161 | 5/1998 |

* cited by examiner

Primary Examiner—John Kim
(74) Attorney, Agent, or Firm—Jane J. Choi; Paula Kelly; Robert M. Barrett (57) ABSTRACT

A dialyzer is provided comprising a casing defining an interior and including a dialysate inlet and a dialysate outlet. A plurality of fibers are located in the interior of the casing and define a fiber bundle. A dialysate inlet fluid channel is provided in fluid communication with the dialysate inlet and includes a plurality of flutes that extend into a portion of the fiber bundles, the flutes define an opening for allowing dialysate to flow from the inlet fluid channel into the interior of the casing. Methods of providing dialysis are also provided.

21 Claims, 2 Drawing Sheets

HEMODIALYZER HAVING IMPROVED DIALYSATE PERFUSION

BACKGROUND OF THE INVENTION

The present invention relates generally to medical treatments. More specifically, the present invention relates to dialysis therapies and dialyzers.

Due to diseases, insult or other causes, the renal system can fail. In renal failure of any cause, there are several physiological derangements. The balance of water, minerals (Na, K, Cl, Ca, P, Mg, $SO_4$) and the excretion of daily metabolic load of fixed hydrogen ions is no longer possible in renal failure. During renal failure, toxic end products of nitrogen metabolism (urea, creatinine, uric acid, and others) can accumulate in blood and tissues.

Dialysis processes have been devised for the separation of elements in a solution by diffusion across a semi-permeable membrane (diffusive solute transport) down a concentration gradient. Principally, dialysis comprises two methods: hemodialysis; and peritoneal dialysis.

Hemodialysis treatment utilizes the patient's blood to remove waste, toxins, and excess water from the patient. The patient is connected to a hemodialysis machine and the patient's blood is pumped through the machine. Catheters are inserted into the patient's veins and arteries to connect the blood flow to and from the hemodialysis machine. Waste, toxins, and excess water are removed from the patient's blood and the blood is infused back into the patient. Hemodialysis treatments last several hours and are generally performed in a treatment center about three to four times per week.

Hemodialysis typically involves the use of a dialyzer. Dialyzers generally comprise a housing or casing. Located within the interior of the casing is a fiber bundle. Typically the fiber bundle is comprised of a number of membranes that are oriented parallel to each other. The membranes are designed to allow blood to flow therethrough with dialysate flowing on the outside of the membranes. Due to an osmotic gradient that is created, waste products are removed from the blood through the membranes into the dialysate.

Accordingly, dialyzers typically include a blood inlet and a blood outlet. The blood inlet is designed to cause blood to enter the fiber membranes and flow therethrough through the blood outlet. Dialysate is designed to flow through an inlet of the dialyzer and out of the dialyzer through an outlet. The dialysate is designed to flow across the outside or exterior walls of the membranes.

One of the issues with prior dialyzers is that the flow of dialysate around the fiber bundles may not be entirely satisfactory. In this regard, dialysate may not flow sufficiently around the entire fiber bundle. Rather shunts between the bundle and the case may occur. This can result in a reduced flow of dialysate around certain portions of membranes contained in the center of the fiber bundle. The clearance of the dialyzer will therefore be reduced.

Accordingly, efforts have been directed at designing dialyzers wherein there is a better perfusion of dialysate into the fiber bundle and specifically the center thereof.

SUMMARY OF THE INVENTION

The present invention provides improved dialyzers and methods for providing dialysis. In this regard, the present invention provides a dialyzer having an improved perfusion of dialysate into the fiber bundle.

To this end, in an embodiment of the present invention, a dialyzer is provided comprising a casing defining an interior and including a dialysate inlet and a dialysate outlet. A plurality of fibers are located in the interior of the casing and define a fiber bundle. A dialysate inlet fluid channel is provided in fluid communication with the dialysate inlet and includes a plurality of flutes that extend into a portion of the fiber bundles, the flutes define an opening for allowing dialysate to flow from the inlet fluid channel into the interior of the casing.

In an embodiment, the dialyzer includes a dialysate outlet fluid channel in fluid communication with the dialysate outlet that includes a plurality of flutes that extend into a portion of the fiber bundle. The flutes define openings for allowing dialysate to flow from the interior of the casing into the dialysate outlet fluid channel.

In an embodiment, the outlet fluid channel and inlet fluid channel have substantially the same structure.

In an embodiment, the casing is constructed from plastic.

In an embodiment, the dialyzer includes eight flutes.

In an embodiment, a top portion of the dialysate inlet is defined by potting material.

In an embodiment, the flutes circumscribe an entire circumference of a first end of the dialyzer.

In an embodiment, the opening in the flutes is a slot.

In an embodiment, each flute defines a separate opening.

In another embodiment of the present invention, a dialyzer is provided comprising a casing defining an interior and having a first end having a dialysate inlet and a second end having a dialysate outlet. A fiber bundle including a plurality of fibers is located within the interior and extends from the first end to the second end. A fluid inlet channel in fluid communication with the dialysate inlet is provided, the fluid inlet channel being defined, in part, by a portion of the casing that defines an exterior surface of the first end and an inner wall that circumscribes a portion of the interior. The inner wall includes portions that extend into the fiber bundle. At least one of the portions includes an aperture for allowing fluid to flow from the channel into the interior. A fluid outlet channel in fluid communication with the dialysate outlet is provided. The fluid outlet channel is defined, in part, by a portion of the casing that defines an exterior surface of the first end and an inner wall that circumscribes a portion of the interior. The inner wall includes portions that extend into the fiber bundle, at least one of the portions including an aperture for allowing fluid to flow from the channel into the interior.

In an embodiment, the inner wall defines a pluality of semicircular structures.

In an embodiment, the fluid inlet channel and fluid outlet channel includes at least six separate portions that extend into the fiber bundle each including an aperture.

In yet another embodiment of the present invention, a dialyzer is provided comprising a casing defining an interior having a fiber bundle located therein and including a first end having a dialysate inlet and a second end having a dialysate outlet. The casing including a dialysate inlet in fluid communication with an inlet fluid channel, the inlet fluid channel defined, at least in part, by an interior wall of the casing, a potting material and an inner wall circumscribing the interior of the first end. The inner wall includes a plurality of members defining areas for receiving fibers of the fiber bundle and a portion that extends into the fiber bundles. Each of the portions of the inner wall that extend into the fiber bundles and include an aperture for allowing dialysate to flow into the interior of the casing.

In an embodiment, the portions define flutes.

In a further embodiment of the present invention, a method for providing dialysis to a patient is provided. The method comprising the steps of passing blood through fiber bundles of a dialyzer and passing dialysate through the dialyzer such that the dialyzer includes portions that separate a portion of the fiber bundle causing more dialysate to flow to an interior of the fiber bundle.

An advantage of the present invention is to provide an improved dialyzer.

A further advantage of the present invention is to provide an improved method of providing dialysis to a patient.

Still further, an advantage of the present invention is to provide an improved housing design for a dialyzer.

Furthermore, an advantage of the present invention is to provide improved fluid flow characteristics in a dialyzer.

Additionally, an advantage of the present invention is to provide a dialyzer having improved efficiency.

Another advantage of the present invention is to provide an improved dialyzer for hemodialysis.

Moreover, an advantage of the present invention is to provide an improved dialyzer that can be used in a number of therapies.

Additional features and advantages of the present invention will be described in and apparent from the detailed description of the presently preferred embodiments and the figures.

DETAILED DESCRIPTION OF THE INVENTION

The present invention provides improved dialyzers and methods of using same. Although in the embodiment set forth below the dialyzer is designed for use in hemodialysis, it should be noted that the dialyzer can be used in a number of different therapies. In this regard, the dialyzer can be used in non-traditional hemodialysis methods. Such methods include, for example, regeneration and continuous flow therapies which may or may not include hemodialysis, for example, continuous flow peritoneal dialysis. Further, although the present invention, in an embodiment, can be utilized in methods of providing dialysis for patients having chronic kidney failure or disease, the present invention can be used for acute dialysis needs, for example, in an emergency room setting.

Figure 1:
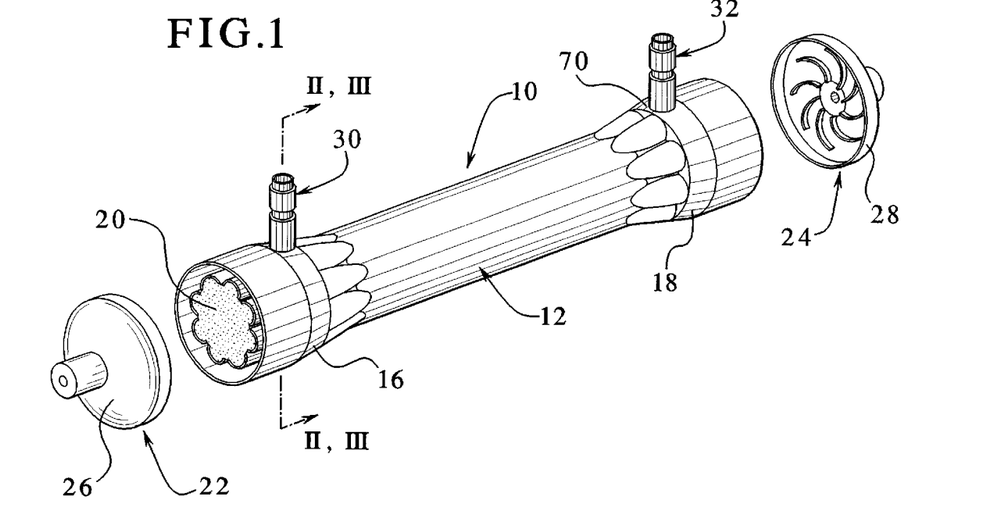
FIG. 1 illustrates a perspective view of an embodiment of a dialyzer of the present invention.
Figure 2:
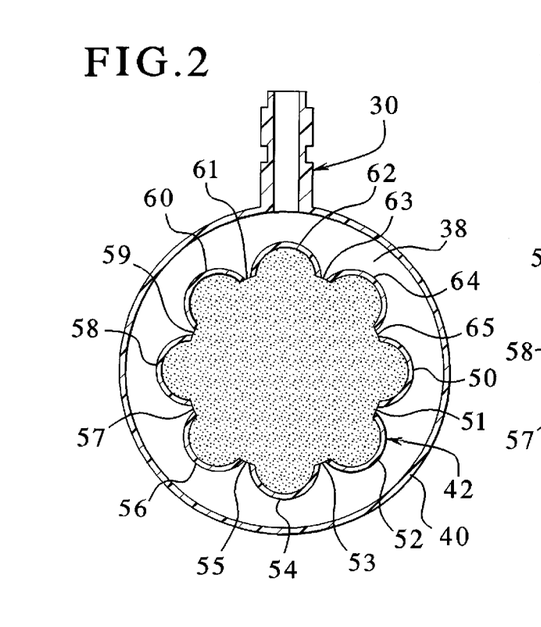
FIG. 2 illustrates a top elevation view of an embodiment of the dialyzer of the present invention.
Figure 3:
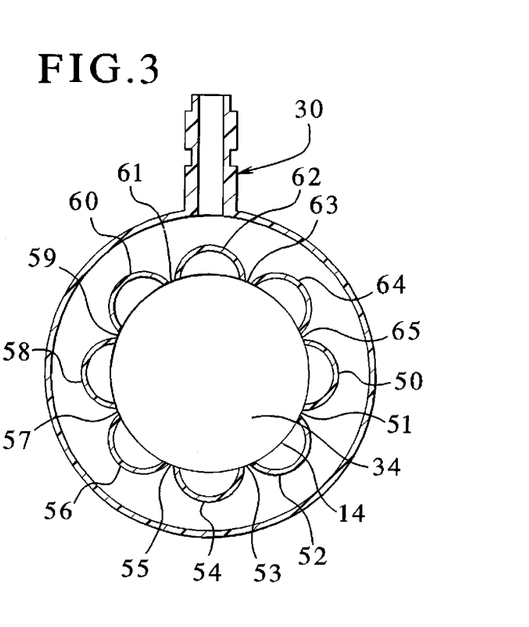
FIG. 3 illustrates the dialyzer of FIG. 2 with the fiber bundle removed.
Figure 4:
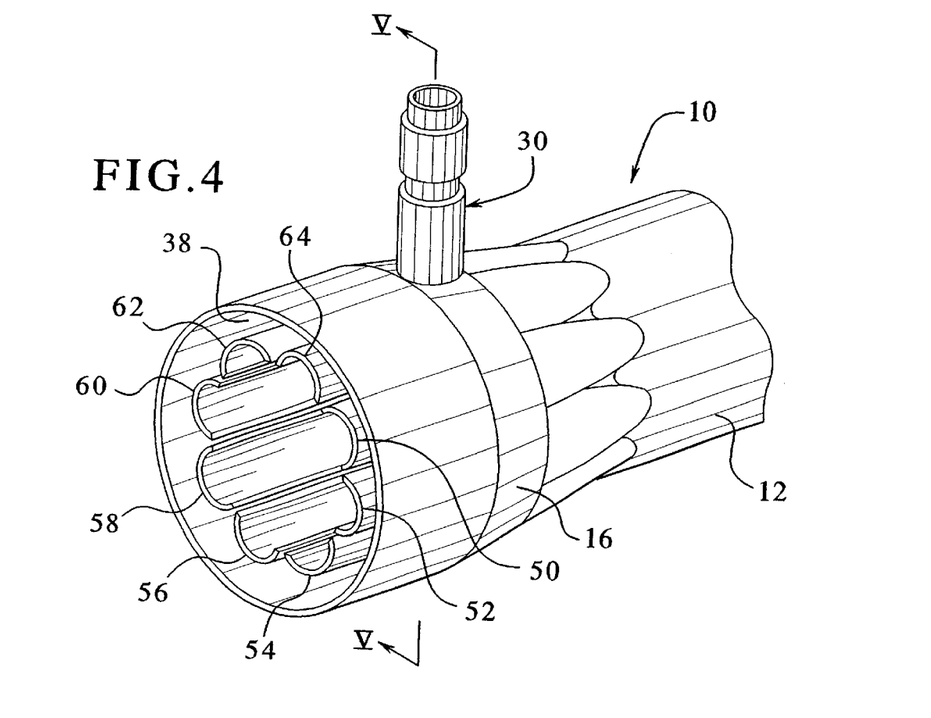
FIG. 4 illustrates a side elevation view of the dialyzer of FIG. 3.
Figure 5:
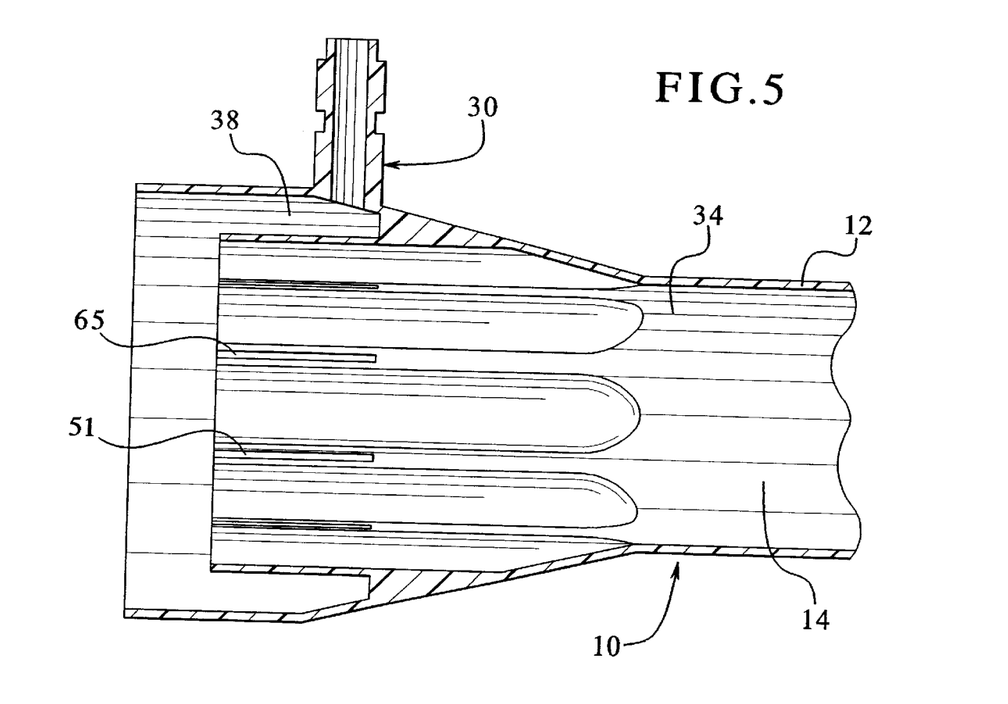
FIG. 5 illustrates a cross-sectional view of the dialyzer of FIG. 4.

Referring now to FIG. 1, a dialyzer 10 is generally illustrated. The dialyzer 10 includes a body member 12 that generally comprises a casing. The casing includes a core section 14 as well as two bell members 16 and 18 located at each end of the dialyzer 10. Located within the core or casing is a fiber bundle 20.

The fiber bundle 20 includes a plurality of hollow fiber membranes. The membranes are semi-permeable having a selective permeability. The membranes are bundled together and assembled in the casing in a manner allowing blood to flow simultaneously in a parallel manner through the lumina of the fibers while a blood cleansing liquid (dialysate) is simultaneously passed through the casing. In theory, this allows the dialysate to bathe the exterior surface of the hollow fibers. A variety of compounds can be used to produce selective permeable membranes including polymers such as: cellulose; cellulose acetate; polyamide; polyacrylonitarile; polyvinyl alcohol; polymethacrylate; polysulfone; and polyolefin. The fiber bundle 20 is encapsulated at each end of the dialyzer to prevent blood flow around the fibers.

Located at a first end of the dialyzer is a fluid inlet 22 and at a second end a fluid outlet 24 defined by a fluid inlet header 26 and a fluid outlet header 28. A variety of header designs can be utilized. In a preferred embodiment the inlet header 26 and outlet header 28 have designs such as those set forth in U.S. patent application Ser. No. 09/871,863 entitled "Hemodialyzer Headers" being filed herewith, the disclosure of which is hereby incorporated by reference. However, any header design can be utilized.

The dialyzer body 10 also includes a dialysate inlet 30 and a dialysate outlet 32. In the preferred embodiment illustrated, the dialysate inlet 30 and dialysate outlet 32 define fluid flow channels that are in a radial direction, i.e., perpendicular to the fluid flow path of the blood. The dialysate inlet 30 and dialysate outlet 32 are designed to allow dialysate to flow into an interior 34 of the dialyzer bathing the exterior surfaces of the fibers and the fiber bundle 20 and then out through the outlet 32. This, as is known in the art, causes waste and other toxins to be removed from the blood through the semipermeable membrane of the fibers and carried away by the dialysate.

Pursuant to the present invention, an improved inlet and/or outlet design is provided. This provides for improved perfusion of the dialysate through the fiber bundle. In this regard, for a hollow fiber dialyzer to function optimally, three mass transfer resistances must be minimized. These mass transfer resistances include: 1) blood resistance; 2) membrane resistance; and 3) dialysate resistance. For a given fiber type and blood flow rate, the blood and membrane resistance are essentially fixed. The dialysate resistance, however, is dictated, in part, by the case design, fiber packing density, and effective shape of the fluid flow path.

In a typical dialyzer, the bells and dialysate inlet and outlet, have straight walls that surround the hollow fiber. Experimental testing, set forth below, reveals the existence of dialysate shunts in such designs. That is, significant axial streams of dialysate flow between the outer surface of the fiber bundle and the core wall of the dialyzer. This results in an inefficient use of dialysate since fluid contact with blood carrying fibers is reduced. In addition, the residence time of the dialysate fluid in the core is short due to the increased flow velocity in these areas. Although experimentally it has been observed that a higher fiber packing density can reduce shunts, an increase in the fiber density makes it more difficult to perfuse dialysate into the center of the bundle.

Set forth in Example 2 are computational fluid dynamic (CFD) studies. These studies demonstrate there is a variation in flow distribution across the diameter of a fiber bundle at various axial locations. It is clear that current designs do not provide sufficient fluid flow into the center of the bundle. This effect is most predominant near the bell/core junction of the case.

The dialysate inlet 30 and dialysate outlet 32 of the dialyzer of the present invention provide a design that reduces shunting. The design also improves dialysate perfusion into the bundle 20. In view of the designs of the present invention, the fiber ends do not deflect outwardly into the chamber of the larger inner diameter of the bell of the core as in prior art designs. Instead, structures are provided causing the outer fibers to be pulled away from the bundle. This provides improved access to the bundle core.

To this end, referring to FIGS. 2–5, the present invention provides an inlet fluid flow channel 38 defined by an outer wall 40, an inner wall 42 and the top wall (not shown) defined by potting material that seals the fiber bundle, as is known in the art. Fluid flows from the dialysate inlet 30 into the inlet fluid channel 38. The inlet fluid channel 34 preferably extends below and above the dialysate inlet 30. Thus, dialysate will enter the inlet fluid channel 34 through the dialysate inlet 30 and flow around the channel into the dialyzer.

As illustrated, the outer wall 40 also defines the exterior of the casing of the dialyzer 10. As noted above, the interior wall 42, with the outer wall 40, defines the inlet flow channel 38. The inner wall also includes a plurality of flutes, in the illustrated embodiment eight flutes 50, 52, 54, 56, 58, 60, 62, and 64. In the preferred embodiment illustrated, these flutes 50, 52, 54, 56, 58, 60, 62, and 64 define semicircular structures. The flutes define openings 51, 53, 55, 57, 59, 61, 63, and 65. In the preferred embodiment illustrated, the opening is a slot shape. However, a variety of openings can be utilized. The openings allow the dialysate that flows through the inlet flow channel 38 to enter an interior 34 of the dialyzer 10.

Due to the structure of the flutes 50, 52, 54, 56, 58, 60, 62, and 64, a portion of the fiber bundle 20 is received within the semi-circular portion of each of the flutes. This causes the bundle 20 to separate below the potting material reducing the fiber density at an area right below the potting material. In addition, this design allows the openings of the flutes to extend into the potting material. Accordingly, dialysate is injected into the bundle as it is received within the inlet channel.

The space between the outer wall 40 of the dialyzer 10 and the inner wall 42 that defines the flutes 50, 52, 54, 56, 58, 60, 62, and 64 is sufficient to allow ample dialysate to flow through the slots 51, 53, 55, 57, 59, 61, and 63 without a significant pressure drop. It should be noted that the slot widths can be varied depending on the position and order of the slots to account for circumferential differences in potting depth that may occur from the potting procedure. This allows the flow rate to be equal at all slot locations.

Although, as illustrated, eight flutes 50, 52, 54, 56, 58, 60, 62, and 64 are provided, and therefore eight openings or slots 51, 53, 55, 57, 59, 61, 63, and 65 more or less flutes can be provided. However, it is believed that eight may be the ideal number.

Preferably, the outlet end 70 of dialyzer 10 includes a structure similar to that of the dialysate inlet. In this regard, the dialysate outlet 70 will include a dialysate outlet channel (not shown) similar to the dialysate inlet flow channel 38. However, this is not necessary and the dialysate outlet 70 can be of a standard bell structure as is known in the prior art. But, certain advantages are achieved by creating the dialysate outlet that is substantially identical to the dialysate inlet, including ease of manufacturing.

By way of example and not limitation, examples of the present invention will now be given.

EXAMPLE No. 1

The following calculations illustrate the effect of dialysate shunts and blood and dialysate maldistributions on dialyzer clearance. Also, set forth below are estimates on the improvement in the clearance of existing dialyzers if the shunts and maldistributions could be eliminated.

The clearance (CL) of a counterflow dialyzer is give by the following equations:

$$CL = Qb\{1 - \exp[(KA/Qb)(1 - Qb/Qd)]\} / \{Qb/Qd - \exp[(KA/Qb)(1 - Qb/Qd)]\}$$

where

K=Overall mass transfer coefficient of the dialyzer for the solute of interest which consists of the mass transfer coefficients (the reciprocal of resistance) on the blood and dialysate sides of the membrane and that of the membrane itself, min/cm A=Area dialyzer, sq.cm.

Qb=Blood flow rate, ml/min.

Qd=Dialysate flow rate, ml/min

If Qb=Qd $$CL = Qb(KA/Qb) / [(KA/Qb) + 1]$$

These equations can be used to calculate the three mass transfer resistances of the standard dialyzers from measured urea clearances. The blood side resistance is 7.6 min/cm, the membrane resistance is 4.6 min/cm, and the dialysate side resistance is 6.4 min/cm.

These equations can also be used to calculate the clearance of a dialyzer to illustrate the effect of shunts and maldistributions of the flows.

Effect of a Dialysate Shunt

If a portion of the dialysate flow does not pass through the fiber bundle of a hollow fiber dialyzer, but shunts between the bundle and the case, the clearance of the dialyzer will be reduced. For analysis purposes we assume that the dialysate flow rate in the above equations is reduced by the amount of the shunt.

Tables 1 and 2 show the reduction in urea clearance with dialysate shunts for a 2.0 square meter and a 2.4 square meter dialyzer. The overall mass transfer coefficient has been adjusted downward to account for the lower dialysate side mass transfer coefficient due to the reduced effective dialysate flow caused by the shunt. It can be seen from these two tables that a large dialysate shunt can dramatically reduce the clearance of a dialyzer. Urea clearance as a function of percentage dialysate shunt for a 2.0 square meter dialyzer with 300 ml/min blood flow and 500 ml/min dialysate flow, is reduced from 269 ml/min to 229 ml/min by a 40% dialysate shunt. For a 2.4 square meter dialyzer, the clearance drops from 278 ml/min to 238 ml/min due to a 40% shunt.

This analysis can also be used to predict the increase in clearance of a dialyzer if a shunt of known magnitude is eliminated. From a measured or calculated clearance value and an assumed shunt magnitude, the overall mass transfer coefficient of the dialyzer can be determined from the preceding equations. Using this calculated value of K and assuming the elimination of the assumed shunt, the improved clearance can be calculated. Table 3 shows the predicted urea clearances of 1.3, 1.6, 1.8 and 2.0 square meter dialyzers where 0%, 10%, 15% and 20% shunt have been eliminated for a blood flow of 300 ml/min and dialysate flow of 500 ml/min.

Effect of Blood and Dialysate Maldistribution.

If the distribution of blood flow through the fibers is not uniform and/or the distribution of dialysate flow through the fiber bundle is not uniform, the clearance of the dialyzer can suffer. Table 4 sets forth the results of four different maldistributions in a 2.0 square meter dialyzer.

In Table 4, Line 1 provides the urea clearance of a dialyzer without maldistributions. Line 2 provides the urea clearance of a dialyzer with blood flow 10% higher. Line 3 is the urea clearance with 10% lower blood flow. In a dialyzer where half the fibers have 10% higher blood flow and the other half have 10% lower blood flow, the clearance of this dialyzer will be the average of the clearances on lines 2 and 3 which is shown on line 4. For a 10% maldistribution of blood flow over the two halves of the dialyzer the urea clearance is only reduced from 268.8 to 267.6 ml/min., a minor reduction.

Lines 5, 6 and 7 of Table 4 set forth a 10% variation in dialysate flow that was added to the 10% blood flow variation with the higher blood flow occurring where the dialysate flow is lower (as what might occur near the center of the bundle). Here the urea clearance dropped further to 265.8 ml/min.

On lines 9 and 10, the dialysate maldistribution is increased to 20%. The urea clearance drops still further to 262.8 ml/min.

On line 11, 12 and 13, 10% variations of blood and dialysate are again considered but, here the maximum blood flow rate occurs where the maximum dialysate flow occurs (as what might happen at the outer portions of the fiber bundle in a dialyzer with a tangential blood inlet header). Here the urea clearance is 268.3 ml/min, almost the same as a dialyzer without any maldistribution.

Using calculations similar to those of Table 4, a 20% maldistribution of both the blood and dialysate will result in a 12 ml/min reduction in clearance reduction in dialyzer clearance for a 2.0 square meter dialyzer at 300 ml/min blood flow and 500 ml/min dialysate flow that can be expected when flow maldistributions of either the blood or dialysate are corrected.

Table 5 provides results similar to Table 4 for a 2.4 square meter dialyzer with a 10% blood maldistribution. Here it is seen that a 20% dialysate shunt reduces the clearance from 276.5 ml/min (line 4) to 271.3 ml/min (line 10).

Table 6 provides similar results for 500 ml/min blood flow and 800 ml/min dialysate flow. Here a 20% dialysate maldistribution results in a clearance reduction from 409.6 ml/min (line 4) to 402.7 ml/min (line 10).

Conclusions

The preceding calculations illustrate that a dialysate shunt can significantly reduce the clearance of a dialyzer. Elimination of dialysate shunts will significantly increase the clearance of a dialyzer.

These calculations also demonstrate that blood and dialysate flow maldistributions can reduce dialyzer clearance significantly. Elimination of flow maldistributions on either the blood side or dialysate side of a dialyzer will improve clearance values.

TABLE 1

Clearance with Dialysate Shunts

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| | Qb = 200 | | | | | | |
| 1 | 200 | 500 | 0.400 | 0.056 | 20000 | 5.600 | 195.773 |
| 2 | 200 | 450 | 0.444 | 0.054 | 20000 | 5.400 | 194.343 |
| 3 | 200 | 400 | 0.500 | 0.052 | 20000 | 5.200 | 192.286 |
| 4 | 200 | 350 | 0.571 | 0.05 | 20000 | 5.000 | 189.221 |
| 5 | 200 | 300 | 0.667 | 0.048 | 20000 | 4.800 | 184.447 |
| 6 | 200 | 250 | 0.800 | 0.046 | 20000 | 4.600 | 176.598 |
| | Qb = 300 | | | | | | |
| 7 | 300 | 500 | 0.600 | 0.056 | 20000 | 3.733 | 268.847 |
| 8 | 300 | 450 | 0.667 | 0.054 | 20000 | 3.600 | 262.313 |
| 9 | 300 | 400 | 0.750 | 0.052 | 20000 | 3.467 | 253.959 |
| 10 | 300 | 350 | 0.857 | 0.05 | 20000 | 3.333 | 243.069 |
| 11 | 300 | 300 | 1.000 | 0.048 | 20000 | 3.200 | 228.571 |
| | Qb = 400 | | | | | | |
| 12 | 400 | 500 | 0.800 | 0.056 | 20000 | 2.800 | 315.849 |
| 13 | 400 | 450 | 0.889 | 0.054 | 20000 | 2.700 | 303.585 |
| 14 | 400 | 400 | 1.000 | 0.052 | 20000 | 2.600 | 288.889 |
| 15 | 400 | 350 | 1.143 | 0.05 | 20000 | 2.500 | 271.063 |
| 16 | 400 | 300 | 1.333 | 0.048 | 20000 | 2.400 | 249.171 |
| | Qb = 500 | | | | | | |
| 17 | 500 | 500 | 1.000 | 0.056 | 20000 | 2.240 | 345.679 |
| 18 | 500 | 450 | 1.111 | 0.054 | 20000 | 2.160 | 328.788 |
| 19 | 500 | 400 | 1.250 | 0.052 | 20000 | 2.080 | 309.300 |
| 20 | 500 | 350 | 1.429 | 0.05 | 20000 | 2.000 | 286.610 |

TABLE 2

Clearance with Dialysate Shunts

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| | Qb = 200 | | | | | | |
| 1 | 200 | 500 | 0.400 | 0.056 | 24000 | 6.720 | 197.856 |
| 2 | 200 | 450 | 0.444 | 0.054 | 24000 | 6.480 | 196.927 |
| 3 | 200 | 400 | 0.500 | 0.052 | 24000 | 6.240 | 195.485 |

TABLE 2-continued

Clearance with Dialysate Shunts

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| 4 | 200 | 350 | 0.571 | 0.05 | 24000 | 6.000 | 193.150 |
| 5 | 200 | 300 | 0.667 | 0.048 | 24000 | 5.760 | 189.167 |
| 6 | 200 | 250 | 0.800 | 0.046 | 24000 | 5.520 | 181.951 |
| | Qb = 300 | | | | | | |
| 7 | 300 | 500 | 0.600 | 0.056 | 24000 | 4.480 | 277.784 |
| 8 | 300 | 450 | 0.667 | 0.054 | 24000 | 4.320 | 271.863 |
| 9 | 300 | 400 | 0.750 | 0.052 | 24000 | 4.160 | 263.929 |
| 10 | 300 | 350 | 0.857 | 0.05 | 24000 | 4.000 | 253.092 |
| 11 | 300 | 300 | 1.000 | 0.048 | 24000 | 3.840 | 238.017 |
| | Qb = 400 | | | | | | |
| 12 | 400 | 500 | 0.800 | 0.056 | 24000 | 3.360 | 330.924 |
| 13 | 400 | 450 | 0.889 | 0.054 | 24000 | 3.240 | 318.367 |
| 14 | 400 | 400 | 1.000 | 0.052 | 24000 | 3.120 | 302.913 |
| 15 | 400 | 350 | 1.143 | 0.05 | 24000 | 3.000 | 283.718 |
| 16 | 400 | 300 | 1.333 | 0.048 | 24000 | 2.880 | 259.714 |
| | Qb = 500 | | | | | | |
| 17 | 500 | 800 | 0.625 | 0.056 | 24000 | 2.688 | 411.352 |
| 18 | 500 | 720 | 0.694 | 0.054 | 24000 | 2.592 | 399.048 |
| 19 | 500 | 640 | 0.781 | 0.052 | 24000 | 2.496 | 384.270 |
| 20 | 500 | 560 | 0.893 | 0.05 | 24000 | 2.400 | 366.196 |

TABLE 3

INCREASE IN CLEARANCE WITH ELIMINATION OF 10%, 15% AND 20% DIALYSATE SHUNT

| Qb | Qd | Kurea | A | Nt | Z | CLurea | Shunt |
|---|---|---|---|---|---|---|---|
| 300 | 500 | 0.054 | 13000 | 2.329 | 0.6 | 238.104 | 0% |
| 300 | 500 | 0.057 | 13000 | 2.472 | 0.6 | 242.527 | 10% |
| 300 | 500 | 0.059 | 13000 | 2.569 | 0.6 | 245.322 | 15% |
| 300 | 500 | 0.062 | 13000 | 2.691 | 0.6 | 248.592 | 20% |
| 300 | 500 | 0.054 | 16000 | 2.867 | 0.6 | 252.898 | 0% |
| 300 | 500 | 0.058 | 16000 | 3.083 | 0.6 | 257.625 | 10% |
| 300 | 500 | 0.061 | 16000 | 3.227 | 0.6 | 260.465 | 15% |
| 300 | 500 | 0.064 | 16000 | 3.410 | 0.6 | 263.773 | 20% |
| 300 | 500 | 0.054 | 18000 | 3.225 | 0.6 | 260.432 | 0% |
| 300 | 500 | 0.058 | 18000 | 3.458 | 0.6 | 264.578 | 10% |
| 300 | 500 | 0.061 | 18000 | 3.634 | 0.6 | 267.375 | 15% |
| 300 | 500 | 0.064 | 18000 | 3.860 | 0.6 | 270.616 | 20% |
| 300 | 500 | 0.054 | 20000 | 3.583 | 0.6 | 266.598 | 0% |
| 300 | 500 | 0.059 | 20000 | 3.923 | 0.6 | 271.442 | 10% |
| 300 | 500 | 0.062 | 20000 | 4.140 | 0.6 | 274.134 | 15% |
| 300 | 500 | 0.066 | 20000 | 4.425 | 0.6 | 277.230 | 20% |

TABLE 4

ANALYSIS OF BLOOD AND DIALYSATE FLOW DISTRIBUTION VARIATIONS

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| | 10% Qb variation, Qd uniform | | | | | | |
| 1 | 300 | 500 | 0.600 | 0.056 | 20000 | 3.733 | 268.847 |
| 2 | 330 | 500 | 0.660 | 0.056 | 20000 | 3.394 | 285.311 |
| 3 | 270 | 500 | 0.540 | 0.056 | 20000 | 4.148 | 249.970 |
| 4 | | | | | | AVERAGE | 267.640 |
| | 10% Qb variation, 10% Qd variation, Qb max where Qd min. | | | | | | |
| 5 | 330 | 450 | 0.733 | 0.056 | 20000 | 3.394 | 279.388 |
| 6 | 270 | 550 | 0.491 | 0.056 | 20000 | 4.148 | 252.314 |
| 7 | | | | | | AVERAGE | 265.851 |
| | 10% Qb variation, 20% Qd variation, Qb max where Qd min. | | | | | | |
| 8 | 330 | 400 | 0.825 | 0.056 | 20000 | 3.394 | 271.436 |
| 9 | 270 | 600 | 0.450 | 0.056 | 20000 | 4.148 | 254.103 |
| 10 | | | | | | AVERAGE | 262.770 |

TABLE 4-continued

ANALYSIS OF BLOOD AND DIALYSATE FLOW DISTRIBUTION VARIATIONS

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| | 10% Qb variation, 10% Qd variation, Qb max. where Qd max. | | | | | | |
| 11 | 300 | 500 | 0.600 | 0.056 | 20000 | 3.733 | 268.847 |
| 12 | 330 | 550 | 0.600 | 0.056 | 20000 | 3.394 | 289.839 |
| 13 | 270 | 450 | 0.600 | 0.056 | 20000 | 4.148 | 246.801 |
| 14 | | | | | | AVERAGE | 268.320 |

TABLE 5

ANALYSIS OF BLOOD AND DIALYSATE FLOW DISTRIBUTION VARIATIONS

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| | 10% Qb variation, Qd uniform | | | | | | |
| 1 | 300 | 500 | 0.600 | 0.056 | 24000 | 4.480 | 277.784 |
| 2 | 330 | 500 | 0.660 | 0.056 | 24000 | 4.073 | 296.344 |
| 3 | 270 | 500 | 0.540 | 0.056 | 24000 | 4.978 | 256.692 |
| 4 | | | | | | AVERAGE | 276.518 |
| | 10% Qb variation, 10% Qd variation, Qd max where Qd min. | | | | | | |
| 5 | 330 | 450 | 0.733 | 0.056 | 24000 | 4.073 | 290.525 |
| 6 | 270 | 550 | 0.491 | 0.056 | 24000 | 4.978 | 258.654 |
| 7 | | | | | | AVERAGE | 274.589 |
| | 10% Qb variation, 20% Qd variation, Qb max where Qd min. | | | | | | |
| 8 | 330 | 400 | 0.825 | 0.056 | 24000 | 4.073 | 282.451 |
| 9 | 270 | 600 | 0.450 | 0.056 | 24000 | 4.978 | 260.102 |
| 10 | | | | | | AVERAGE | 271.277 |
| | 10% Qb variation, 10% Qd variation, Qb max. where Qd max. | | | | | | |
| 11 | 300 | 500 | 0.600 | 0.056 | 24000 | 4.480 | 277.784 |
| 12 | 330 | 550 | 0.600 | 0.056 | 24000 | 4.073 | 300.662 |
| 13 | 270 | 450 | 0.600 | 0.056 | 24000 | 4.978 | 253.937 |
| 14 | | | | | | AVERAGE | 277.300 |

TABLE 6

ANALYSIS OF BLOOD AND DIALYSATE FLOW DISTRIBUTION VARIATIONS

| Line | Qb (ml/min) | Qd (ml/min) | Z = Qb/Qd | K (min/cm) | A (cm**2) | Nt = KA/Qb | CL (ml/min) |
|---|---|---|---|---|---|---|---|
| | 10% Qb variation, Qd uniform | | | | | | |
| 1 | 500 | 800 | 0.625 | 0.056 | 24000 | 2.688 | 411.352 |
| 2 | 550 | 800 | 0.688 | 0.056 | 24000 | 2.444 | 432.162 |
| 3 | 450 | 800 | 0.563 | 0.056 | 24000 | 2.987 | 387.128 |
| 4 | | | | | | AVERAGE | 409.645 |
| | 10% Qb variation, 10% Qd variation, Qb max where Qd min. | | | | | | |
| 5 | 550 | 720 | 0.764 | 0.056 | 24000 | 2.444 | 422.278 |
| 6 | 450 | 880 | 0.511 | 0.056 | 24000 | 2.987 | 392.013 |
| 7 | | | | | | AVERAGE | 407.145 |
| | 10% Qb variation, 20% Qd variation, Qb max where Qd min. | | | | | | |
| 8 | 550 | 640 | 0.859 | 0.056 | 24000 | 2.444 | 409.551 |
| 9 | 450 | 960 | 0.469 | 0.056 | 24000 | 2.987 | 395.897 |
| 10 | | | | | | AVERAGE | 402.724 |
| | 10% Qb variation, 10% Qd variation, Qb max. where Qd max. | | | | | | |
| 11 | 500 | 800 | 0.625 | 0.056 | 24000 | 2.688 | 411.352 |
| 12 | 550 | 880 | 0.625 | 0.056 | 24000 | 2.444 | 440.011 |
| 13 | 450 | 720 | 0.625 | 0.056 | 24000 | 2.987 | 380.836 |
| 14 | | | | | | AVERAGE | 410.423 |

EXAMPLE No. 2

A computational fluid dynamics (CFD) analysis was performed for the blood and dialysate flow transport phenomena occurring in dialyzers of various designs. This experiment assumed that there is no mass-transfer (ultrafiltration) between the blood and the dialysate flows through the porous fiber wall. The two flow fields were analyzed separately. Several different housing variations and header designs were considered. A porous medium model was used to simulate the flow in the fiber bundle. The flow permeability for the fiber-bundle was computed from a CFD model.

This study concluded that in general the blood flow distributions in the fiber-bundle are fairly uniform. But a flow stagnant region usually exists in the inlet header. A flattened header design can greatly reduce the flow stagnant region.

The dialysate flow distributions are quite non-uniform for the regions adjacent to the flow inlet and outlet. However, the distributions of dialysate flow for the dialyzer header designs of the present invention are more uniform than the conventional dialyzer.

There are thousands of fibers in a dialyzer. It is not feasible to solve for the detailed flow distribution around each fiber. A porous medium model is used here for modeling the over-all flow and pressure distributions in the fiber-bundle. The model assumes that there is a local balance between pressure and resistance forces in the flow domain such that:

$$-K_i U_i = \partial p / \partial \xi_i,$$

where (i=1,2,3) represents the orthotropic directions (three mutually orthogonal principal axes with differening material properties or conditions). $K_i$ is the permeability and $U_i$ is the superficial velocity in direction $\zeta_i$. (The volume flow rate divided by the total cross-sectional area.) The permeability $K_i$ is computed by the following equation:

$$K_i = \alpha_i |\hat{U}| + \beta_i$$

where $\alpha_i$ and $\beta_i$ are constants for a particular flow, $\hat{U}$ is the superficial velocity vector. It is noted that the permeability in Darcy's law is defined as:

$$-\mu U_i = \kappa_i \partial p / \partial \xi_i$$

where $\kappa_i$ is the permeability and is equal to $\mu/K_i$.

The flow in the dialyzer is assumed to be laminar, steady state, incompressible, and Newtonian. The permeability for the porous-medium flow model should be derived from the flow pressure drop in the fiber-bundle measured experimentally. However, the experimental data are not available. The other alternative is to solve for the pressure distributions numerically. First it is assumed that the fibers are arranged in a fixed staggered pattern. The space in between the fibers is computed from the given fiber packing factor.

The blood flow in a dialyzer is inside the hollow fibers. The porous medium flow permeability along the axial-direction is computed based on the pressure drop for a fully developed laminar pipe flow. The permeability is infinite for cross flow.

For the dialysate flow outside the fibers, the pressure drop is computed numerically for flow in several layers of fibers. Then the flow permeability is calculated from the computed pressure gradient for the particular fiber configuration. The axial flow pressure drop is different from the cross-flow pressure drop and the flow in each direction is computed separately.

It is noted that the porous medium model is only an approximation for the actual complicated flow problem. The fiber distributions in a dialyzer are usually non-uniform and the flow permeability varies spatially.

In this study, two dialyzer designs were analyzed. The first is an elongated version of the prior art dialyzer and the second is the present invention dialyzer. The input parameters for both cases are presented in Table 7.

In the elongated prior art dialyzer, dialysate is introduced to the bundle in the inlet bell, where all the fibers along the bundle perimeter are exposed. In the present invention dialyzer, there are eight slots in the inlet bell region through which dialysate is introduced to adjacent sections of the fiber bundle. The width and length of the slots are 0.031" and 0.294", respectively. The bell configurations for the opposite (outlet) end of each dialyzer are the same as the respective inlets.

The output values are presented in Table 8. For the elongated present art dialyzer, it is seen that the dialysate flow velocity is not very uniform adjacent to the flow inlet and outlet and there is a 50% difference between the maximum and the minimum values. The velocity profiles are more uniform in the mid-section of the bundle, with about a 2% difference between the maximum and minimum values.

For the present invention dialyzer at a dialysate flow rate of 500 ml/min, the dialysate flow velocity is uniform adjacent to the flow inlet and outlet showing a 6% difference between the maximum and the minimum values. In the mid-section of the bundle, there exists a 0.5% flow variation. Flow characteristics for this dialyzer are also shown for a dialysate flow rate of 1000 ml/min.

Conclusions

This study has shown that the dialysate flow in the present invention dialyzer is more uniform than in the elongated prior art dialyzer. This is especially true for the flow adjacent to the dialysate inlet and outlet.

TABLE 7

Input parameters for various runs (dialysate side)

| Run Name | Elongated Prior Art Dialyzer | Present Invention Dialyzer | |
|---|---|---|---|
| Fiber parameters | | | |
| ID ($\mu$m) | 200 | 200 | |
| OD ($\mu$m) | 260 | 260 | |
| Wall thickness ($\mu$m) | 30 | 30 | |
| Number of fibers | 11,200 | 11,200 | |
| Effective fiber length (cm) | 32.6 | 31.55 | |
| Dialyzer surface area (m$^2$) | 2.3 | 2.3 | |
| Fiber packing factor | | | |
| Straight section | 0.483 | 0.537 | |
| Bell | 0.483 | 0.306 | |
| Permeability | | | |
| Parallel flow (kg/m$^3$ s) | 8.348 × 10$^6$ | 8.348 × 10$^6$ | |
| Cross flow (kg/m$^3$ s) | Infinite | Infinite | |
| Dialysate parameters | | | |
| $Q_d$ (ml/min) | 500 | 500 | 1000 |
| Porosity | | | |
| Straight section | 0.517 | 0.463 | |
| Bell | 0.517 | 0.694 | |
| Dialysate viscosity (cp) | 1 | 1 | |
| Dialysate density (kg/m$^3$) | 1000 | 1000 | |
| Permeability (kg/m$^3$ s) | | | |
| Straight section (cross-flow) | 9.65 × 10$^5$ | 2.51 × 10$^6$ | |
| Bell (cross-flow) | 9.65 × 10$^5$ | 6.02 × 10$^5$ | |
| Straight section (parallel flow) | 1.37 × 10$^6$ | 2.25 × 10$^6$ | |
| Bell (parallel flow) | 1.37 × 10$^6$ | 1.45 × 10$^6$ | |

TABLE 8

Output values for various runs (dialysate side)

| Run Name | Elongated prior art dialyzer | Present invention dialyzer | |
|---|---|---|---|
| $Q_d$ (ml/min) | 500 | 500 | 1000 |
| Pressure drop (mmHg) | 20.1 | 45.78 | 92.55 |
| Maximum shear rate (1/s) | | | 1407 |
| Maximum % flow maldistribution | | | |
| Near inlet | 50 | 6 | 0.7 |
| Midplane | 2 | 0.5 | 0.8 |
| Near outlet | 50 | 4 | 1.1 |

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A dialyzer having a fluid inlet and a fluid outlet comprising:
   a casing defining an interior and including a dialysate inlet and a dialysate outlet wherein the casing is in fluid communication with the fluid inlet and the fluid outlet;
   a plurality of fibers located in the interior of the casing and defining a fiber bundle; and
   a dialysate inlet fluid channel in fluid communication with the dialysate inlet and including a plurality of flutes that extend into a portion of the fiber bundles, the flutes defining an opening for allowing dialysate to flow from the inlet fluid channel into the interior of the casing.

2. The dialyzer of claim 1 including a dialysate outlet fluid channel in fluid communication with the dialysate outlet and including a plurality of flutes that extend into a portion of the fiber bundle, the flutes defining openings for allowing dialysate to flow from the interior of the casing into the dialysate outlet fluid channel.

3. The dialyzer of claim 2 wherein the outlet fluid channel and inlet fluid channel have substantially the same structure.

4. The dialyzer of claim 1 wherein the casing is constructed from plastic.

5. The dialyzer of claim 1 including eight flutes.

6. The dialyzer of claim 1 wherein a top portion of the dialysate inlet fluid channel is defined by potting material.

7. The dialyzer of claim 1 wherein the flutes circumscribe an entire circumference of a first end of the dialyzer.

8. The dialyzer of claim 1 wherein the opening in the flutes is a slot.

9. The dialyzer of claim 8 wherein each flute defines a separate opening.

10. A dialyzer having a fluid inlet and a fluid outlet comprising:
    a casing defining an interior and having a first end having a dialysate inlet and a second end having a dialysate outlet wherein the casing is in fluid communication with the fluid inlet and the fluid outlet;
    a fiber bundle including a plurality of fibers located within the interior and extending from the first end to the second end;
    a fluid inlet channel in fluid communication with the dialysate inlet, the fluid inlet channel being defined in part by a portion of the casing that defines an exterior surface of the first end and an inner wall that circumscribes a portion of the interior, the inner wall including portions that extend into the fiber bundle, at least one of the portions including an aperture for allowing fluid to flow from the fluid inlet channel into the interior; and
    a fluid outlet channel in fluid communication with the dialysate outlet, the fluid outlet channel being defined in part by a portion of the casing that defines an exterior surface of the second end and an inner wall that circumscribes a portion of the interior, the inner wall including portions that extend into the fiber bundle, at least one of the portions including an aperture for allowing fluid to flow from the interior into the fluid outlet channel.

11. The dialyzer of claim 10 wherein the inner wall defines a plurality of semicircular structures.

12. The dialyzer of claim 10 wherein the outlet fluid channel and inlet fluid channel have substantially the same structure.

13. The dialyzer of claim 10 wherein a top portion of the fluid inlet channel is defined by potting material.

14. The dialyzer of claim 10 wherein the aperture is a slot.

15. The dialyzer of claim 10 wherein the fluid inlet channel and fluid outlet channel includes at least six separate portions that extend into the fiber bundle each including an aperture.

16. A dialyzer having a fluid inlet and a fluid outlet comprising:
    a casing defining an interior and including a first end having a dialysate inlet and a second end having a dialysate outlet wherein the casing is in fluid communication with the fluid inlet and the fluid outlet;
    a fiber bundle located in the interior of the casing; and
    a dialysate inlet in fluid communication with an inlet fluid channel, the inlet fluid channel defined, at least in part, by an interior wall of the casing, a potting material and an inner wall circumscribing the interior of the first end and including a plurality of members defining areas for receiving fibers of the fiber bundle and a portion that extends into the fiber bundles, each of the portions extending into the fiber bundles including an aperture for allowing dialysate to flow into the interior of the casing.

17. The dialyzer of claim 16 wherein the portions define flutes.

18. The dialyzer of claim 16 wherein the second end includes a dialysate outlet fluid channel including a plurality of flutes that extend into a portion of the fiber bundle, the flutes including openings for allowing dialysate to flow from the interior of the casing into the dialysate outlet fluid channel.

19. The dialyzer of claim 18 wherein the outlet fluid channel and inlet fluid channel have substantially the same structure.

20. The dialyzer of claim 17 including eight flutes.

21. The dialyzer of claim 17 wherein the opening in the flutes is a slot.

* * * * *